(12) United States Patent
Miyazaki et al.

(10) Patent No.: US 7,695,737 B2
(45) Date of Patent: Apr. 13, 2010

(54) SPHERICAL COMPOSITE PARTICLES AND COSMETICS WITH THE PARTICLES BLENDED THEREIN

(75) Inventors: Takumi Miyazaki, Kitakyushu (JP); Hirokazu Tanaka, Kitakyushu (JP)

(73) Assignee: JGC Catalysts & Chemocals Ltd., Kawasaki-shi, Kanagawa-ken (JP)

( * ) Notice: Subject to any disclaimer, the term of this patent is extended or adjusted under 35 U.S.C. 154(b) by 1998 days.

(21) Appl. No.: 10/379,720

(22) Filed: Mar. 6, 2003

(65) Prior Publication Data

US 2003/0215474 A1 Nov. 20, 2003

Related U.S. Application Data

(63) Continuation-in-part of application No. 09/789,842, filed on Feb. 22, 2001, now abandoned.

(30) Foreign Application Priority Data

Mar. 8, 2000 (JP) .............................. 2000-064117

(51) Int. Cl.
 *A61K 9/14* (2006.01)
 *C08K 3/10* (2006.01)
(52) U.S. Cl. ...................... 424/489; 514/951; 524/413
(58) Field of Classification Search ................. 424/489, 424/449–501, 486, 426, 488; 428/402; 514/944, 514/909, 779, 951; 524/413
See application file for complete search history.

(56) References Cited

U.S. PATENT DOCUMENTS

| | | | | | |
|---|---|---|---|---|---|
| 3,846,453 | A | * | 11/1974 | Erneta | ......................... 524/791 |
| 5,122,418 | A | * | 6/1992 | Nakane et al. | .............. 424/401 |
| 5,288,790 | A | * | 2/1994 | Nakahara et al. | ............ 524/495 |
| 5,902,569 | A | * | 5/1999 | Oshima et al. | ................. 424/59 |
| 5,939,079 | A | * | 8/1999 | Le Royer et al. | ............ 424/401 |
| 6,740,590 | B1 | * | 5/2004 | Yano et al. | ................... 438/692 |

OTHER PUBLICATIONS

Corneliussen, http://www.maropolymeronline.com/Properties/modulus_values.asp, obtained on Jan. 9, 2009, pp. 1-11.*

* cited by examiner

*Primary Examiner*—Johann R Richter
*Assistant Examiner*—Abigail Fisher
(74) *Attorney, Agent, or Firm*—Manabu Kanesaka

(57) ABSTRACT

Spherical composite particles are formed of inorganic fine particles and resin fine particles joined together, and an average particle diameter is in the range from 1.1 to 100 μm, in which the average particle diameter of the inorganic fine particles is in the range from 5 to 600 nm and the average particle diameter of the resin fine particles is in the range from 10 to 500 nm. The inorganic fine particle and the resin fine particle have almost the same size, and the hardness, softness, and adaptability when spreading on a skin can finely be adjusted as desired in a wide range according to the contact feeling required for the cosmetics in which the particles are blended.

5 Claims, No Drawings

SPHERICAL COMPOSITE PARTICLES AND COSMETICS WITH THE PARTICLES BLENDED THEREIN

CROSS-REFERENCE TO RELATED APPLICATION

This is a continuation in part application of Ser. No. 09/789,842 filed on Feb. 22, 2001 now abandoned.

BACKGROUND OF THE INVENTION AND RELATED ART STATEMENT

The present invention relates to spherical composite particles comprising inorganic fine particles and resin fine particles each having the substantially same size, and to cosmetics with the spherical composite particles blended therein and enabling optimization of feeling in use thereof such as dry feeling, creaminess, easiness in being spread on skin, and smoothness.

Conventionally, spherical particles of inorganic oxides such as silica, titanium oxide, and alumina, spherical particles of the inorganic oxides each having an organic group, or spherical particles of resin based on such materials as PMMA, nylon, silicone, and polystyrene have been blended in make-up cosmetics such as powder foundation or cosmetics for skin such as milky lotion. The effect obtained by blending the spherical particles in the cosmetics is improvement in the feeling of smoothness in use provided by rolling of the spherical particles on human skin.

In the case of particles of inorganic oxides, the hardness is high, so that mainly the dry feeling is obtained, and in the case of particles of resin, as the hardness is relatively low, soft feeling is obtained in use. This feeling in use is influenced not only by an average diameter of the spherical particles and distribution of the particle diameters, but also by physical or chemical characteristics of substances each constituting the particles. Specifically the feeling in use of the particles as cosmetics is influenced by, in addition to the hardness of the particles, the chemical characteristics of substances constituting the particles. For instance, nylon having an amide bond is well adapted to human skin and insures the feeling of smoothness in use.

When classified according to the hardness of the particles, among the particles for cosmetics currently commercially available in the marker, those having relatively high flexibility include particles of silicone rubber, while hard ones include particles of inorganic oxide particles such as silica. Hardness of particles of resin such as PMMA, polystyrene, silicone, and nylon is between the two types of particles described above.

Hardness of resin particles can be adjusted to some extent by adjusting the molecular structure by bridging or other means or by blending components for improving the softness, but adjustment of hardness of the particles in a wide range is impossible, and therefore it has been difficult to obtain spherical particles having the desired softness or hardness.

Japanese Patent Laid-Open Publication No. SHO 62-234008, Japanese Patent Laid-Open Publication No. SHO 62-181211, and Japanese Patent Laid-Open Publication No. HEI 3-18140 disclose use of spherical particles having disruptiveness under pressurized conditions as a means for improving the feeling in use such as adaptability to being spread on human skin. For instance, Japanese Patent Laid-Open Publication No. HEI 3-18140 proposes spherical particles with disruptiveness under pressurized conditions and having the shear breaking strength in the range from 10 to 260 g/cm$^2$ formed by spraying-drying slurry-like material comprising particles for cosmetics and an inorganic colloidal solution dispersed in a dispersion medium at pre-specified respective ratio, and cosmetics for skin with the particles blended therein. Because the spherical particles with disruptiveness under pressurized conditions gradually collapse due to the shearing stress when the cosmetics are applied and spread on human skin, the particles are effective in improving adaptability of the cosmetics to being spread on skin as well as in weight reduction. However, the hardness and softness of particles vary according to conditions for preparation of the cosmetics and for each type of cosmetics, and it is required to freely adjust the hardness and softness, or the disruptiveness under pressurized conditions of the spherical particles. Further as the spherical particles gradually collapse during use of the cosmetics, there is also the problem that the conventional types of cosmetics can not insure the dry feeling or the feeling of creaminess obtained when the spherical particles roll without collapsing.

SUMMARY OF THE INVENTION

The present invention was made to solve the problems as described above, and it is an object of the present invention to provide spherical composite particles adjusted to the desired hardness, softness, and adaptability to be spread smoothly according to a degree of contact feeling required for the cosmetics in which the particles are blended. It is another object of the present invention to provide cosmetics with the spherical composite particles blended therein and having the desired softness, smoothness, and adaptability to be spread on skin.

The present invention provides spherical composite particles comprising inorganic fine particles and resin fine particles joined together and the average particle diameter is in the range from 0.5 to 100 μm, i.e. 1.1 to 100 μm, in which the average particle diameter of the inorganic fine particles is in the range from 5 to 600 nm and the average particle diameter of the resin fine particles is in the range from 10 to 500 nm. The spherical composite particle comprises an inorganic fine particle and a resin fine particle each having almost the same size, joined to each other, and the hardness, softness, and adaptability to being spread on skin can finely be adjusted to desired ones in a wide range respectively according to the contact feeling required for the cosmetics in which the particles are blended.

The resin fine particles should preferably comprise resin having elasticity like rubber with the 100% modulus during tension in the range from 200 to 3000 N/cm$^2$. The spherical composite particles can be obtained by spraying-drying a dispersion obtained by dispersing the inorganic fine particles and the resin fine particles in water and/or an organic solvent. It is preferable to obtain spherical composite particles by further heating the spherical composite particles obtained in the above spraying-drying step under the temperature of glass transition of the resin or more.

In the cosmetics according to the present invention, the spherical composite particles are blended therein in the range from 0.1 to 80 weight %. The cosmetics described above can be optimized in its feeling in use such as dry feeling, creaminess, adaptability in being spread, and smoothness by blending the spherical composite particles.

DETAILED DESCRIPTION OF PREFERRED EMBODIMENTS

Preferable embodiments of the present invention are described below. The average particle diameter of the spherical composite particles according to the present invention is in the range from 0.5 to 100 µm, preferably 1.1 to 100 µm, and more preferably in the range from 1.1 to 20 µm. When the average particle diameter of the spherical composite particles is less than 0.5 µm, the particles are too small and are not adapted to being spread on human skin, and on the contrary when the average particle diameter is more than 100 µm, the particles are too large to lost the feeling of smoothness. The blending ratio of inorganic fine particles in the spherical composite particles is preferably in the range from 0.5 to 99.5 weight %, and more preferably in the range from 20 to 99 weight %.

When the blending ratio of the inorganic fine particles is low in the above-described range, the hardness is higher than that of the spherical resin particles comprising only fine particles of resin, but the feeling of smoothness equivalent to that of the spherical resin particles can be obtained, and when the blending ratio is high in the range, the particles are more soft as compared to the spherical inorganic particles comprising only the inorganic fine particles, but the feeling of dry feeling equivalent to the spherical inorganic particles can be obtained.

Any of known resin fine particles may be used as the resin fine particles in the present invention, and resin particles selected from the group consisting of polyurethane, styrene-butadiene copolymer, acrylonitrile-butadiene copolymer, those having elasticity like rubber such as nylon-based, polyester-based, polyolefin-based, and silicone-based elastomers, synthetic high polymers such as nylon, polyester, polyolefin, polymethyl methacrylate (PMMA), vinyl acetate/acrylic acid ester copolymer, ethylene/vinyl acetate copolymer, acrylic acid ester, polyvinyl alcohol, polystyrene, cellulose and derivatives thereof, and natural high polymers such as Cyamoposis gum may be used. Two or more selected from this group may be mixed in use.

When it is desired to make the flexibility higher, it is preferable to use, in the compositions listed above, polyurethane, styrene-butadiene copolymer, acrylonitrile-butadiene copolymer, or compositions having elasticity like rubber such as nylon-based, polyester-based, polyolefin-based, and silicone-based elastomer, and is also preferable to use resin fine particles having the rubber-like elasticity with the 100% modulus in tension in the range from 200 to 3000 $N/cm^2$. Further it is preferable that extendability up to disruption is in the range from 100 to 800%.

The 100% modulus and extension in disruption can be measured through the extension test as described below. At first, a resin is applied by the doctor-blade method, then the resin is dried to form a film with the thickness of 30 µm, and the film is punched out to form an H-shaped film for testing. The right and left edges of this H-shaped film for testing are pulled at the tensile rate of 20 mm/minute to obtain the relation between the extension (cm) and stress (load (N)/cross section area ($cm^2$)). The term of "100% modulus" indicates the stress ($N/cm^2$) when the film for testing is extended to the length two times longer than the original length, while the term of "extension in disruption" is the extension (cm) of the film for testing when it is extended to be disrupted.

There is no specific restrictions over a method of manufacturing the resin fine particles so long as particles each with the diameter in the range from 10 to 500 nm and preferably 10-200 nm, can be obtained, and the method includes polymerization by emulsification, polymerization by suspension, the method of emulsifying and dispersing polymer previously polymerized, and polymerization by deposition using an amphiphile polymer.

The average particle diameter of the resin fine particles as described above is in the range from 10 to 500 nm, and is preferably in the range from 20 to 400 nm. When the average particle diameter of the resin fine particles is less than 10 nm, the dispersion stability when the resin fine particles are dispersed in a solvent is rather low and the sphericity of obtained composite particles is poor, so that sometimes its adaptability to rolling becomes lower and the desired effects (such as creaminess, softness, or the like) may not be obtained when the particles are blended in the cosmetics. When the average particle diameter is more than 500 nm, agglomeration between resin particles or between the resin particles and inorganic fine particles becomes harder to occur, and sometimes spherical composite particles can not be obtained after the step of spraying-drying described below, and even when the spherical composite particles can be obtained, as joint points between the particles are few, collapse of particles easily occurs when a pressure is loaded to the particles, which makes it difficult to maintain the constant feeling in use such as smoothness. In addition, also in this case, the sphericity of the spherical composite particles is apt to become lower with the rolling capability also becoming lower, which may make it difficult to obtain the excellent feeling in use such as smoothness.

The above resin particles added in addition to reactive functional groups such as various alkoxyl, silanol, epoxy, isocyanate, carboxyl, oxazoline may be used in the present invention. The resin particles having the functional groups can strengthen the combination between the resin fine particles or between the resin fine particles and the inorganic fine particles. Further these resin particles can decrease the solubility for various solvents and the imbibition of obtained composite particles.

The inorganic fine particles, which can be used in the present invention, includes, but not limited to, fine particles of oxides such as those of silica, alumina, titanium oxide, zirconia, zinc oxide, iron oxide, cerium oxide, magnesium oxide, and fine particles of composite oxides of these compositions. Further fine particles of oxides and composite oxides each having an organic group may be used in this invention. Any of these compositions may be used in singularity or, two or more of the compositions may be mixed in use. Further inorganic fines particles which carry a metal component such as silver, copper, or zinc can be used on the inorganic substance.

Further metallic fine particles such as those of gold, silver, copper, palladium, platinum, fine particles of alloy, and those of composite metals may be used as the inorganic fine particles. When inorganic oxides capable of absorbing ultraviolet ray such as titanium oxide, zinc oxide, and cerium oxide are used, the ultraviolet ray shielding effect is provided. When iron oxide or magnesium oxide is used, it is possible to give the deodorizing effect or to obtain colored particles. Further, when inorganic fine particles with a metallic component such as silver, copper, and zinc carried thereon are used, antibacterial effect is given. When metallic fine particles, fine particles of alloys, or those of composite metals are used, it is possible to give the infrared ray shielding effect or to obtain colored spherical composite particles.

The average particle diameter of the inorganic fine particles is in the range from 5 to 600 nm, and preferably is in the range from 10 to 100 nm. When the average particle diameter of the inorganic fine particles is less than 5 nm, the inorganic fine particles are apt to coagulate with each other, which makes it difficult to uniformly blend resin fine particles and inorganic fine particles, and also strength and hardness of obtained composite particles are insufficient, so that disruption easily occurs when a pressure is loaded thereto and constant feeling in use can not be maintained. When the average particle diameter is more than 600 nm, the number of joint points between the inorganic fine particles or between the inorganic fine particles and resin fine particles becomes smaller, although the degree depends on the size of resin fine particles blended therein, so that disruption of the fine particles easily occurs and constant feeling such as cleanliness can not be maintained. Further, the sphericity of the spherical composite particles becomes lower with the capability of rolling also becoming lower, so that the excellent feeling of sufficient smoothness can not be obtained.

As the inorganic fine particles as described above, it is advantageous to use sol of silica, i.e. silica sol, proposed by the present applicant (Japanese Patent Laid-Open Publication No. SHO 63-45114), sol of silica composite material, i.e. silica-base composite sol (Japanese Patent Laid-Open Publication No. HEI 5-132309), sol of titanium, i.e. titania sol (Japanese Patent Laid-Open Publication No. SHO 63-185820, Japanese Patent Laid-Open Publication No. SHO 63-229139), sol of zirconium, i.e. zirconia sol (Japanese Patent Laid-Open Publication No. HEI 2-48418), and metallic fine particles (Japanese Patent Laid-Open Publication No. HEI 10-188681, Japanese Patent Laid-Open Publication No. HEI 11-12608).

Further in addition to the inorganic fine particles and resin fine particles as described above, compounds having a specific function such as a ultraviolet ray absorbent or a moisture retention agent may be used in singularity or in the mixed state, and the specific function as described above can be added to the fine particles by processing the spherical composite particles with the ultraviolet ray absorbent or the moisture retention agent.

As the method of giving the specific function as described above to resin fine particles, it is possible to incorporate an organic group having a specific function such as the ultraviolet ray absorbing capability, or moisture retention capability in the resin by means of graft polymerization, or to give the specific function to polymerized resin by means of chemical treatment. The ultraviolet ray absorbing substances include, but not limited to, an organic ultraviolet absorbent, and an inorganic ultraviolet ray shielding agent, while the moisture retention agent includes, for instance, glycerin. Further it is possible to use resins having bridge structures between polymer molecules or between polymer molecules and inorganic fine particles to improve the resistance of the resin against a solvent.

There is no specific restriction over a combination of inorganic fine particles and resin fine particles constituting the spherical composite particles according to the present invention. When fine particles having high flexibility are required, it is preferable to use such resin particles as those of polyurethane, styrene-butadiene copolymer, acrylonitrile-butadiene copolymer, or rubber-like ones having elasticity such as nylon-based, polyester-based, polyolefin-based, and silicone-based elastomer. Further when the feeling of smoothness well adapted to human skin is required, it is advantageous to use particles of nylon or nylon-based elastomer as the fine particles of resin. As the inorganic fine particles, fine particles of silica, alumina, and magnesium oxide are preferable when the excellent feeling of transparency is required, while inorganic fine particles having high refractive index such as titanium oxide, zirconia, or zinc oxide are preferable when a chromaticity or the high shielding capability is desired. Further when colored spherical composite particles having a specific color such as red or yellow are desired, it is preferable to use fine particles such as those of iron oxide and cerium oxide.

The spherical composite particles according to the present invention should preferably be spherical composite particles obtained by spraying-drying a dispersion in which aforesaid inorganic fine particles with the average particle diameter in the range from 5 to 600 nm and aforesaid resin fine particles with the average particle diameter in the range from 10 to 500 nm are dissolved in water and/or an organic solvent. As the organic solvent, it is possible to use such a solvent as methanol, ethanol, iso-propyl alcohol, n-propyl alcohol, toluene, xylene, methylethyl ketone, acetone, chloroform, or dimethyl sulfoxide. When a dispersion medium of the dispersion is water, it is preferable to use the various types of resin described above in the latex or emulsion form (with the particle diameter in the range from 10 to 500 nm in either case). As a dispersant such as a surface surfactant may give negative effects to dispersion of other components in some types of cosmetics, it is advised that the dispersant is not mixed in the cosmetics.

It is possible to select a solvent appropriate for dissolving each of the resins described above and to use a solution in which the resin is uniformly dissolved in place of the dispersion, and also it is possible to use a mixture of a solution in which resin is dissolved and the dispersion. Water or organic solvents may be selected according to the dispersion characteristics and solubility of resin as the dispersion medium used in a dispersion of the resin fine particles according to the present invention, but when the cost performance or influence to environment is taken into considerations, it is preferable to use water as the dispersion medium.

The spherical composite particles according to the present invention can be obtained by spraying-drying a dispersion in which the inorganic fine particles and resin fine particles are mixed. Employment of the spraying-drying method is preferable because there is no specific limitation over the dispersion medium to be used for the method and also because particles with excellent sphericity and uniform particle diameter can be obtained. As the apparatus for spraying-drying the dispersion, various types of sprayers/dryers based on the disk rotation system or the nozzle system may be used.

The total concentration of inorganic fine particles and resin fine particles in the dispersion should preferably be in the range from 2 to 50 weight %, and more specifically in the range from 10 to 30 weight %. When the total concentration is less than 2 weight %, a percentage of fine particles each having the diameter of 0.5 µm or less becomes higher with the production efficient becoming lower, so that use of the dispersion is not preferable. On the other hand, when the total concentration is more than 50 weight %, viscosity of the dispersion is too high to obtain spherical composite particles each having a small particle diameter, and also distribution of the particle diameters is too wide to be used for the purpose according to the present invention.

Spherical composite particles having the desired size can be obtained by selecting a concentration of a mixed dispersion of the inorganic fine particles and resin fine particles, a concentration of a solution in which the inorganic fine particles and resin fine particles are dissolved, and condition for spraying-drying the dispersion or the solution. For drying, usually the temperature substantially equal to the boiling point of the solvent can be used, but the temperature may be either higher or lower as compared to a boiling point of the solvent so long as dry spherical composite particles can be obtained. The spherical composite particles obtained as described above have voids based on clearances between fine particles or between the inorganic fine particles and resin fine particles, and also have excellent flexibility.

Further by heating the obtained spherical composite particles under the substantially same temperature as the glass transition temperature of the resin, the bond between the resin fine particles or between the resin fine particles and inorganic fine particles is further promoted. In this case, even if a pressure is loaded to the spherical composite particles as described above, the particles seldom collapse, so that, when the spherical composite particles treated as described above are blended in cosmetics, the constant feeling in use (such as dry feeling, smoothness, or adaptability to being spread) is given to the cosmetics. When the temperature for treating the spherical composite particles is high, it is possible also to obtain spherical composite particles with reduced voids or without any void therein.

Next the cosmetics according to the present invention is described below. It is preferable that the spherical composite particles are blended in the cosmetics according to the present invention at a rate in the range from 0.1 to 80 weight %, and more preferably in the range from 2 to 30 weight %. When the blending rate of the spherical composite particles is less than 0.1 weight %, any specific effect can not be obtained by blending the particles in the cosmetics, and when the blending rate is more than 80 weight %, the characteristics such as coloring, covering, and adaptability to being uniformly spread which are originally required for cosmetics becomes lower. When the spherical composite particles are blended within the range described above, it is possible to obtain the cosmetics having the feeling of smoothness and well adapted to being spread on human skin which gives the desired comfortable feeling in use such as dry feeling and creaminess. For instance, when an emulsion is used, even if spherical composite particles with inorganic fine particles blended therein at a high ratio are used, it is possible to obtain cosmetics not giving a sense of incongruity and insuring the feeling of smoothness because of rolling of the spherical composite particles like in the case where silica particles not containing resin fine particles are used. On the contrary, even when spherical composite particles with resin fine particles blended therein at a high ratio are used, the feeling of softness and smoothness and well adaptability to being spread on human skin can be given to cosmetics with the spherical composite particles blended therein like in the case when resin fine particles not containing inorganic fine particles are used.

Further also when used in powder foundation, the sense of incongruity when spread on human skin with a puff is reduced and the smoothness and well adaptability to being spread are more excellent as compared to the case where silica particles containing resin particles a little or not containing resin particles at all are used. It should be noted that, when the spherical composite particles according to the present invention are blended in cosmetics, surface treatment may be performed with silicone or fluorine to the spherical composite particles according to the necessity before the spherical composite particles are blended in the cosmetics.

The cosmetics according to the present invention contains at least one of various components usually blended in cosmetics such as, for instance, high molecular weight aliphatic alcohol; high molecular weight aliphatic acid; oils such as ester oil, paraffin oil, and wax; alcohol such as ethyl alcohol, propylene glycohol, sorbitol, and glycerin; moisture retention agents such as mucosaccharides, collagens, PCA (2-pyrrolidone-5-carboxylic acid) salt, and lactates; various types of surface surfactants such as nonion-based, cation-based, anion-based, and amphoteric ones; various types of gums such as Arabian gum, xanthane gum, polyvinyl pyrrolidone, ethyl cellulose, carboxymethyl cellulose, carboxyvinyl polymer, denatured or not-denatured clay minerals; solvents such as ethyl acetate, acetone, and toluene; inorganic pigments and dyes, organic pigments and dyes; antioxidants such as BHT, and tocopherol; water; chemicals; ultraviolet ray absorbents; pH buffers; chelating agents; antiseptics; and fragrant chemicals. Also at least one of inorganic fillers such as silica, talc, kaolin, and mica, extenders, and various types of organic resins may be contained therein. Further, alumina, and phosphor oxide may be contained.

The cosmetics according to the present invention can be manufactured in the ordinary way, and may be used in various forms such as powder, cake, pencil-like form, stick, liquid, and cream. More specifically the forms include foundation, cream, emulsion, eye-shadow, basement for cosmetics, nail enamel, eye liner, mascara, lip-stick, pack, cosmetic water, shampoo, rinse, and hair cosmetics.

EXAMPLES

Examples 1 to 5

As the fine particles of resin, aqueous dispersion (self-emulsifying type, concentration of solid components of 30 weight %, and particle diameter of 60 nm) of polycarbonate-based polyurethane not turning yellow which has glass transition temperature of 90° C., the tensile extension of 380% and 100% modulus of 1400 N/cm$^2$ measured at 30 μm thickness film was used, and as the inorganic fine particles, silica sol with the particle diameter of 15 nm (produced by C.C.I.C., Cataloid S-30L, with the silica concentration of 30 weight %) was used. The silica sol and polyurethane aqueous dispersion were mixed so that the silica/polyurethane weight ratio is 98/2 (Example 1), 95/5 (Example 2), 90/10 (Example 3), 50/50 (Example 4), or 20/80 (Example 5), and a specified quantity of water was added so that the total concentration of inorganic fine particles and resin fine particles (described as solid component concentration) was 20 weight %. The liquid prepared as described above was sprayed under the dry atmosphere with the humidity of 5% and the temperature of 70° C. and the powder was collected. Further this powder was heated for 8 hours under the temperature of 100° C. The resultant spherical composite particles were observed with a scan type of electron microscope, and the substantial sphericity was observed. The average particle diameters and 10% K value are as shown in Table 1. The result of sensuality assessment when the obtained composite powder was spread on human skin is shown in Table 1. The 10% K value varies in association with change of a mixing ratio of silica and polyurethane, and also the tactile feeling gradually changed from a hard one to a soft one.

The average particle diameter of the spherical composite particles was measured by taking a picture of the particles with a scan type electron microscope (manufactured by Nippon Denshi, JSM-5300), and analyzing 200 particles on this picture with an image analyzers (manufactured by Asahi Kasei, IP-100). The 10% K value (compression elasticity modulus) of spherical composite particles was measured with a minute compression tester (manufactured by Shimazu Seisakusho, MCTM-201) as a measurement gauge by using one fine particle with the particle diameter of D as a sample, adding a load at a constant loading rate to the sample, deforming the particle up to a level where the compression displacement reaches 10% of the particle diameter, and measuring the load and compression displacement (mm) when the particle was displaced by 10%. The 10% K value was obtained by substituting the particle diameter D as well as the compression load and compression displacement into the following equation (1). In this embodiment, the 10% K value was measured for 10 particles and the average was calculated.

As for the specific conditions for measurement, assuming the compression rate constant was 1, the loading rate was changed in the range from 0.28 to 2.67 mN/sec according to the particle diameter with the maximum test load set to 0.1N.

$$K=(3/2^{1/2}) \times F \times S^{-3/2} \times (D/2)^{-1/2} \quad (1)$$

wherein F indicates a load value (N) when the particle was compressed and deformed by 10%; S indicates the compression displacement (mm) when the particle was compressed and deformed by 10%, and D indicates the particle diameter (mm).

[Sensuality Testing Method] The sensuality assessment was performed using the obtained powders by 20 female panellers. The assessment was performed by taking a small quantity of each powder on the inside of the upper part of their arms, rubbing the sample with fingers, and assessing the feeling of incongruity, lightness, and smoothness.

[Control 1] Only the same silica sol as that used in Example 1 was used, and water was added so that the silica concentration was adjusted to 20 weight %, and spraying-drying, and heating were performed under the same conditions as those in Example 1. The average particle diameter, 10% K value, and result of the sensuality test are shown in Table 1.

[Control 2] Only the aqueous dispersion of the same polyurethane resin fine particles as those used in Example 1 was used, water was added to the dispersion so that the solid component concentration was 20 weight %, and spraying-drying, and heating were performed under the same conditions as those in Example 1. The average diameter, 10% K value and result of the sensuality test are shown in Table 1.

TABLE 1

| Exa./Con. | Inorganic fine particles/resin fine particles (wt. ratio) | Average particle diameter (μm) | 10% K value (N/mm²) | Sensuality test |
|---|---|---|---|---|
| Example 1 | 98/2 | 5.9 | 13940 | Hard, and dry feeling |
| Example 2 | 95/5 | 5.9 | 5600 | Hard, and slight dry feeling |
| Example 3 | 90/10 | 5.8 | 2630 | Soft, and feeling of rolling |
| Example 4 | 50/50 | 5.4 | 1410 | Soft, and extending extending smoothly |
| Example 5 | 20/80 | 5.3 | 960 | Very soft, and low sense of incongruity |
| Control 1 | Silica | 5.9 | 19500 | Very hard, and dry feeling |
| Control 2 | Poly-urethane | 5.3 | 650 | Very soft, no sense of incongruity |

Examples 6 to 10

An aqueous dispersion (self-emulsifying type with the solid component concentration of 40% and particle diameter of 90 nm) of styrene-butadiene copolymer which has glass transition temperature of 58° C., the tensile extension of 310% and the 100% modulus 2100 N/cm² measured at 30 μm thickness film was used as the resin fine particles, and titanium oxide sol with the particle diameter of 60 nm (produced by C.C.I.C., Sunveil PW-6030 with the solid component concentration of 30% and containing silica at the solid component ratio of 13%) was used as inorganic fine particles. The titanium oxide sol and styrene-butadiene copolymer aqueous dispersion were mixed with each other so that the weight-based mixing ratio of titanium oxide vs styrene-butadiene copolymer was 98/2 (Example 6), 95/5 (Example 7), 90/10 (Example 8), 50/50 (Example 9), or 20/80 (Example 10), and further a specified quantity of water was added to the mixture so that the solid component concentration was 20%. The liquid prepared as described above was sprayed under the dry atmosphere with the humidity of 5% and the temperature of 70° C. and the powder was collected. This powdered particles were observed with a scan type electron microscope, and the substantial sphericity was observed. Diameters of 200 particles were measured, and the average particle diameters were as shown in Table 2. Also the measured 10% K values and results of sensuality assessment when the particles were spread on human skin were as shown in Table 2. The 10% K value changes in association with change in the mixing ratio of titanium oxide vs styrene-butadiene copolymer, and also the tactile feeling changed from hardness to softness. As compared to the silica/polyurethane particles obtained in Example 1, the general achromaticity was higher. When the sample with the titanium oxide blending ratio of 50% was dispersed in glycerin so that the concentration was 1%, and the transmission factor was measured with the spectrophotometer (produced by Hitachi, Model U-2000), and it was confirmed that the transmission factor lowered for the wavelength of 350 nm or below and that the preparation had the ultraviolet ray shielding effect.

[Control 3] Only the same titanium oxide sol as that used in Example 6 was used, water was added to the sol so that the solid component concentration was 20%, and spraying-drying, and heating were performed under the same conditions as those in Example 6. The average particle diameter, 10% K value and result of sensuality test are as shown in Table 2.

[Control 4] only the same aqueous dispersion of styrene-butadiene copolymer as that used in Example 6 was used, water was added to the aqueous dispersion so that the solid component concentration was 20%, and spraying-drying, and heating were performed under the same conditions as those in Example 6. the average particle diameter, 10% K value and result of sensuality test are as shown in Table 2.

TABLE 2

| Exa./Con. | Inorganic fine particles/resin fine particles (wt. ratio) | Average particle diameter (μm) | 10% K value (N/mm²) | Sensuality test |
|---|---|---|---|---|
| Example 6 | 98/2 | 7.0 | 14810 | Hard, and heavy smoothness |
| Example 7 | 95/5 | 7.0 | 11600 | Hard, and heavy dry feeling |
| Example 8 | 90/10 | 7.4 | 7050 | Hard, and feeling of rolling |
| Example 9 | 50/50 | 7.6 | 1950 | Soft, and extending smoothly |
| Example 10 | 20/80 | 7.8 | 1310 | Very soft, and smooth |
| Control 3 | Titanium oxide | 6.8 | 16200 | Very hard, and heavy |
| Control 4 | Copolymer resin | 8.3 | 910 | Very soft, no sense of incongruity |

Examples 11 to 15

An aqueous dispersion (anion-based dispersion type of emulsion with the solid component concentration of 45% and particle diameter of 140 nm) of PMMA (polymethyl methacrylate) which has glass transition temperature of 45° C., the tensile extension of 40% measured with 30 μm thickness film was used as resin particles, and an iron oxide-titanium oxide composite sol with the particle diameter of 10 nm (produced by C.C.I.C., Sunveil F, iron oxide/titanium oxide=50/50, containing silica at the solid component ratio of 13% and the solid component concentration of 15%) was used as inorganic. fine particles. The iron oxide-titanium oxide composite compound and the PMMA aqueous dispersion were mixed with each other so that the weight-based mixing ratio of iron oxide-titanium composite compound vs PMMA was 98/2 (Example 11), 95/5 (Example 12), 90/10 (Example 13), 50/50 (Example 14), and 20/80 (Example 15), and further a specified quantity of water was added to the mixture so that the solid component concentration was 15%. This preparation liquid was sprayed and dried in the atmosphere with the humidity of 5% at the temperature of 70° C., and the produced dark red powder was collected. Further this powder was heated for 8 hours under 80° C. These powdered particles were observed with a scan type electron microscope, and the substantial sphericity was observed. Diameters of 200 particles were measured, and the average diameters were as shown in Table 3. Measured 10% K values and results of sensuality when the particles were spread on human skin are as shown in Table 3. The 10% K values changed in association with change in the iron oxide/titanium oxide composite compound and PMMA blending ratio, and also the tactile feeling gradually changes from hardness to softness. As the PMMA itself has a relatively high 10% K value, it is necessary to blend the PMMA at the blending ratio of 10% or more to improve the feeling in use.

[Control 5] Only the same iron oxide titanium oxide sol as that used in Example 11 was used, and spraying-drying, and heating were performed under the same conditions as those in Example 11. The average particle diameters, 10% K values and result of sensuality test are as shown in Table 3.

[Control 6] Only the same aqueous dispersion of PMMA as that used in Example 11 was used, and water was added to the dispersion so that the solid component concentration was 20%, and then spraying-drying, and heating were performed under the same conditions as those in Example 11. The average particle diameter, 10% K value and result of sensuality test are as shown in Table 3.

TABLE 3

| Exa./Con. | Inorganic fine particles/resin fine particles (wt. ratio) | Average particle diameter (μm) | 10% K value (N/mm²) | Sensuality test |
|---|---|---|---|---|
| Example 11 | 98/2 | 5.1 | 18550 | Very hard, and heavy |
| Example 12 | 95/5 | 5.1 | 16690 | Very hard, and dry feeling |
| Example 13 | 90/10 | 5.3 | 13550 | Hard, and dry feeling |
| Example 14 | 50/50 | 5.3 | 6210 | Hard, and light dry feeling |
| Example 15 | 20/80 | 5.6 | 5360 | Slightly hard, and dry feeling |
| Control 5 | Inorganic composite sol | 5.0 | 20100 | Very hard, and heavy |
| Control 6 | PMMA | 5.6 | 4800 | A little hard, and dry feeling |

Example 16, Example 17

Emulsions were prepared by blending the following raw materials A to C at the respective ratios (weight %) shown below. Both the raw materials A and B were Heated to 80° C. and dissolved, and then the raw material B was gradually added stirring to the raw material A to emulsify the mixture. Then the mixtures were cooled stirring to 40° C., and then the raw material C was added, the mixtures were homogenized, stirring was stopped, and the reaction mixtures were left for a while to obtain emulsions.

| Raw Material A. | |
|---|---|
| Monostearic acid polyoxymethylene sorbitan | 1.0 |
| Tetraoleic acid polyoxyethylene sorbitol | 1.5 |
| Monostearic acid glyceryl | 1.5 |
| Stearic acid | 0.5 |
| Biphenyl alcohol | 1.0 |
| Palmitic acid cetyl | 0.5 |
| Squalane | 5.0 |
| 2-ethyl hexane acid cetyl | 4.0 |
| Methyl polysiloxane | 0.5 |
| Antiseptic | As required |
| Raw Material B. | |
| 1,3-butylene glycol | 10.0 |
| Xanthane gum | 0.1 |
| Purified water | 69.4 |
| Raw Material C. | |
| Spherical composite particles | 5.0 |

The emulsions were prepared by blending the spherical composite particles obtained in Example 3 (silica/polyurethane=90/10) and the spherical composite particles obtained in Example 4 (silica/polyurethane=50/10) respectively as raw material C. The two types of emulsions were applied on human skin for comparing the respective tactile feeling to each other. As a result, in the emulsion blended 90/10 composite particles (Example 16), it was felt that the composite spherical particles were rolling and the adaptability to be spread on human skin was excellent, and in the emulsion blended 50/50 composite particles (Example 17), the feelings of softness and smoothness were obtained, and also the adaptability to being spread on human skin was excellent. As described above, the different feeling in use was obtained according to the different blending ratio.

[Control 7] An emulsion was obtained by blending the spherical silica obtained in Control 1 in place of the spherical composite particles obtained in Example 4 following the same sequence as that in Example 17. As compared to the emulsion in Example 17, in the case of this emulsion, it was strongly felt, when this emulsion was applied to human skin, that the spherical particles were rolling, and it was felt that the sense of integrity with other components of the emulsion had been lost.

[Control 8] An emulsion was obtained by blending the spherical polyurethane obtained in Control 2 in place of the spherical composite particles obtained in Example 4 following the same sequence as that in Example 17. As compared to the emulsion in Example 17, when this emulsion was applied to human skin, the feeling of incongruity was not sensed at all, and the feeling in use completely different from that in Example 17 was obtained.

Example 18, Example 19

The following raw materials A and B were blended to form powder foundations so that a blending ratio of each component (weight %) was as shown below. The raw material A was homogenized by stirring, and also the raw material B was fully stirred to homogenize it under the elevated temperature of 70° C. Then the raw material A was added to the raw material B, And the mixtures were stirred to homogenize it, and then the mixtures were pulverized, compressed and molded. Raw Material A.

| Raw Material A. | |
|---|---|
| Titanium oxide | 10.7 |
| Colcothar | 0.55 |
| Yellow iron oxide | 2.55 |
| Black iron oxide | 0.15 |
| Talc | 20.0 |
| Mica | 22.1 |
| Sericite | 28.0 |
| Spherical composite particles | 8.0 |
| Raw Material B. | |
| Silicone oil | 3.0 |
| Squalane | 3.2 |
| Myristyl myristate | 1.6 |
| Sorbitan sesquiolate | 0.2 |
| Aroma chemical | As required |
| Antiseptic | As required |

The emulsions were prepared by blending the spherical composite particles obtained in Example 8 (titanium oxide/styrene butadiene copolymer=90/10) and the spherical composite particles obtained in Example 9 (titanium oxide/styrene butadiene copolymer=50/10) respectively. When the emulsion blended 90/10 composite particles (Example 18) was spread on skin, it was felt that the spherical particles were rolling in the powder foundation and the adaptability to being spread on human skin was excellent, but when the emulsion blended 50/50 composite particles (Example 19) was spread on skin, it was felt that the powder foundation was wet and smooth. When the blending ratio was changed, also the feeling in use changed.

[Control 9] A powder foundation was obtained by following the same sequence as that in Example 19 except the point that the spherical titanium oxide particles obtained in Control 3 were blended in place of the spherical composite particles obtained in Example 9. The tactile feeling when the powder foundation was applied on human skin was rather poorer in terms of the adaptability to being spread on human skin as compared to the powder foundation in Example 19.

[Control 10] A powder foundation was obtained by following the same sequence as that in Example 19 except the point that the spherical styrene-butadiene copolymer particles obtained in Control 4 were blended in place of the spherical composite particles obtained in Example 9. When the powder foundation was applied on skin, different from the foundation in Example 19, the feeling of incongruity was not felt, and the feeling in use was different from that when the foundation in Example 19 was applied.

Examples 20-24

The respective spherical composite particles obtained in the same manner as in Examples 1-5 were classified by the air elutriation to obtain new spherical composite particles having smaller average particle diameters.

The respective obtained spherical composite particles were observed by the scan type electron microscope, so that spherical particles of an almost complete spherical shape were found, and their average particle diameters are shown in table 4. Incidentally, the 10% K values thereof are the same as those of corresponding Examples 1-5.

Also, the tests for the sensuality assessment were carried out by applying the obtained composite powders to human skin, and the results of the sensuality assessment are shown in Table 4 wherein the hard feeling was changed to the soft feeling in correspondence with increase in polyurethane resin rate.

[Control 11] The silica particles obtained in the same manner as in Control 1 were classified by the air elutriation to obtain new silica particles having a smaller average particle diameter. The results of the average particle diameter, 10% K value and sensuality test are shown in Table 4.

[Control 12] The polyurethane particles obtained in the same manner as in Control 2 were classified by the air elutriation to obtain new polyurethane particles having a smaller average particle diameter. The results of the average particle diameter, 10% K value and sensuality test are shown in Table 4.

TABLE 4

| Exa./Con. | Inorganic fine particles/resin fine particles (wt. ratio) | Average particle diameter (μm) | 10% K value (N/mm$^2$) | Sensuality test |
|---|---|---|---|---|
| Example 20 | 98/2 | 2.3 | 13940 | Hard, dry, and light feeling |
| Example 21 | 95/5 | 2.3 | 5600 | Hard, dry, and light feeling |
| Example 22 | 90/10 | 2.0 | 2630 | Soft, and smooth |
| Example 23 | 50/50 | 1.6 | 1410 | Soft, smooth, and wet |
| Example 24 | 20/80 | 1.1 | 960 | Very soft, wet, no sense of incongruity |
| Control 11 | silica | 2.1 | 19500 | Very hard, dry, and light feeling |
| Control 12 | polyurethane | 1.0 | 650 | Very soft, and no sense of incongruity |

Examples 25-29

The respective spherical composite particles obtained in the same manner as in Examples 6-10 were classified by the air elutriation to obtain new spherical composite particles having a smaller average particle diameter.

The respective obtained spherical composite particles were observed by the scan type electron microscope, so that spherical particles of an almost complete spherical shape were found, and their average particle diameters are shown in table 5. Incidentally, the 10% K values thereof are the same as those of corresponding Examples 6-10.

Also, the tests for the sensuality assessment were carried out by applying the obtained composite powders to human skins, and the results of the sensuality assessment are shown in Table 5, wherein the hard feeling was changed to the soft feeling in correspondence with increase in titanium oxide and styrene-butadiene copolymer. Also, when the sample with the titanium oxide blending ratio of 50% was dispersed in glycerin so that the concentration became 1 wt %, and the transmission factor was measured with a spectrophotometer (produced by Hitachi, Model U-2000), and it was confirmed that the transmission factor was lowered for the wavelength of 350 nm or below and that the preparation had the ultraviolet ray shielding effect.

[Control 13] The titanium oxide particles obtained in the same manner as in Control 3 were classified by the air elutriation to obtain new titanium oxide particles having a smaller average particle diameter. The results of the average particle diameter, 10% K value and sensuality test are shown in Table 5.

[Control 14] The copolymer resin particles obtained in the same manner as in Control 4 were classified by the air elutriation to obtain new copolymer resin particles having a smaller average particle diameter. The results of the average particle diameter, 10% K value and sensuality test are shown in Table 5.

TABLE 5

| Exa./Con. | Inorganic fine particles/resin fine particles (wt. ratio) | Average particle diameter (μm) | 10% K value (N/mm$^2$) | Sensuality test |
|---|---|---|---|---|
| Example 25 | 98/2 | 2.4 | 14810 | Hard, heavy, and slightly dry feeling |
| Example 26 | 95/5 | 2.4 | 11600 | Hard, slightly heavy, and dry feeling |
| Example 27 | 90/10 | 1.5 | 7050 | Hard, slightly heavy, and smooth |
| Example 28 | 50/50 | 1.5 | 1950 | Soft, and smooth |
| Example 29 | 20/80 | 1.5 | 1310 | Very soft, and wet feeling |
| Control 13 | Titanium oxide | 2.7 | 16200 | Very hard, and very heavy feeling |
| Control 14 | Copolymer resin | 1.3 | 910 | Very soft, no sense of incongruity |

Examples 30-34

The respective spherical composite particles obtained in the same manner as in Examples 11-15 were classified by the air elutriation to obtain new spherical composite particles having a smaller average particle diameter.

The respective obtained spherical composite particles were observed by the scan type electron microscope, so that spherical particles of an almost complete spherical shape were found, and their average particle diameters are shown in table 6. Incidentally, the 10% K values thereof are the same as those of corresponding Examples 11-15.

Also, the sensuality assessment tests were carried out by applying the obtained composite powders to human skins, and the results of the sensuality assessment are shown in Table 6.

The feeling gradually changed in association with change in the iron oxide-titanium oxide composite compound and PMMA blending ratio from the hardness to the softness. As the PMMA itself had a high 10% K value, it was necessary to blend the PMMA at the blending ratio of 10% or more to improve the feeling in use.

[Control 15] The iron oxide-titanium oxide inorganic composite particles obtained in the same manner as in Control 5 were classified by the air elutriation to obtain new titanium-oxide particles having a smaller average particle diameter. The results of the average particle diameter, 10% K value and sensuality test are shown in Table. 6.

[Control 16] The PMMA resin particles obtained in the same manner as in Control 6 were classified by the air elutriation to obtain new copolymer resin particles having a smaller average particle diameter. The results of the average particle diameter, 10% K value and sensuality test are shown in Table 6.

TABLE 6

| Exa./Con. | Inorganic fine particles/resin fine particles (wt. ratio) | Average particle diameter (μm) | 10% K value (N/mm$^2$) | Sensuality test |
|---|---|---|---|---|
| Example 30 | 98/2 | 2.5 | 18550 | Very hard, and heavy feeling |
| Example 31 | 95/5 | 2.5 | 16690 | Very hard, and slightly dry feeling |
| Example 32 | 90/10 | 2.5 | 13550 | Hard, and dry feeling |
| Example 33 | 50/50 | 2.5 | 6210 | Hard, slightly light and dry feeling |
| Example 34 | 20/80 | 2.4 | 5360 | Slightly hard, and light dry feeling |
| Control 15 | Inorganic composite sol | 2.5 | 20100 | Very hard, and heavy feeling |
| Control 16 | PMMA | 1.8 | 4800 | Slightly hard, and light dry feeling |

Examples 35, 36

Cosmetic Materials

In Examples 35, 36, the emulsions were prepared in the same manner except that the spherical composite particles obtained in Examples 22, 23 were used. Both emulsions were applied to human skins for comparing the respective tactile feelings thereof. In the emulsion of 90/10, i.e. Example 35, smooth and soft feelings of the composite spherical particles and light application feeling were obtained. On the other hand, in the emulsion of 50/50, i.e. Example 36, the soft and smooth feelings were obtained and there was no sense of incongruity when applied. The different feelings were obtained depending on the blending ratios of both particles.

[Control 17] The emulsion was prepared under the same condition except that the spherical silica obtained in Control 11 was blended instead of the composite spherical particles of Example 36. The feeling when applied to the human skin was compared with that of Example 36, and it was found that there were less soft feeling, an incongruity sense and no uniting sense with other emulsion's component.

[Control 18] The emulsion was prepared under the same condition except that the spherical polyurethane obtained in Control 12 was blended instead of the composite spherical particles of Example 36. The feeling when applied to the human skin was compared with the emulsion prepared in Example 36. No incongruity was sensed, and the feeling different from that of Example 35 was obtained.

What is claimed is:

1. A spherical composite particles having an average particle diameter in a range from 1.1 to 100 μm, and formed of inorganic particles having an average particle diameter in a range from 5 to 600 nm, and resin particles joined with the inorganic particles and having an average particle diameter in a range from 10 to 200 nm, said resin particles being formed of a resin having elasticity with stress in a range from 200 to 3000 N/cm$^2$ when a film of the resin is extended to a length two times longer than the original length, wherein said resin particles are selected from the group consisting of polyurethane, styrene-butadiene copolymer, and polymethyl methacrylate.

2. The spherical composite particles according to claim 1, wherein an amount of the inorganic particles in the spherical composite particles is in a range from 0.5 to 99.5 weight %.

3. The spherical composite particles according to claim 2, wherein said average particle diameter of the inorganic particles is in a range from 10 to 100 nm.

4. A cosmetic comprising the spherical composite particles according to claim 1 in a range from 0.1 to 80 weight %, and a material used as the cosmetic.

5. The spherical composite particles according to claim 1, wherein said average particle diameter of the spherical composite particles is between 5.1 and 100 μm.

* * * * *